(12) United States Patent
Makker et al.

(10) Patent No.: US 6,254,607 B1
(45) Date of Patent: Jul. 3, 2001

(54) IOL INSERTION APPARATUS AND METHOD FOR USING SAME

(75) Inventors: Harish C. Makker, Mission Viejo; Shih-Liang S. Yang, Laguna Hills; Daniel G. Brady, San Juan Capistrano, all of CA (US)

(73) Assignee: Allergan, Waco, TX (US)

( * ) Notice: Subject to any disclaimer, the term of this patent is extended or adjusted under 35 U.S.C. 154(b) by 0 days.

(21) Appl. No.: 09/392,066

(22) Filed: Sep. 8, 1999

Related U.S. Application Data

(62) Division of application No. 09/253,639, filed on Feb. 19, 1999, now Pat. No. 6,093,193, which is a division of application No. 08/864,296, filed on May 28, 1997, now Pat. No. 5,876,407, which is a division of application No. 08/592,753, filed on Jan. 26, 1996, now Pat. No. 5,735,858.

(51) Int. Cl.[7] ........................................ A61F 9/00
(52) U.S. Cl. ............................................. 606/107
(58) Field of Search ............................. 606/107

(56) References Cited

U.S. PATENT DOCUMENTS

| | | |
|---|---|---|
| 4,681,102 | 7/1987 | Bartell . |
| 4,785,810 | 11/1988 | Buccala et al. . |
| 4,834,094 | 5/1989 | Patton et al. . |
| 4,836,201 | 6/1989 | Patton et al. . |
| 4,919,130 | 4/1990 | Stoy et al. . |
| 4,934,363 | 6/1990 | Smith et al. . |
| 5,190,552 | 3/1993 | Kelman . |
| 5,304,182 | 4/1994 | Rheinish et al. . |
| 5,451,229 | * 9/1995 | Geuder et al. ................ 606/107 |
| 5,474,562 | 12/1995 | Orchowski et al. . |
| 5,494,484 | 2/1996 | Feingold . |
| 5,496,328 | 3/1996 | Nakajima et al. . |
| 5,499,987 | 3/1996 | Feingold . |
| 5,535,746 | 7/1996 | Hoover et al. . |
| 5,551,448 | 9/1996 | Matula et al. . |
| 5,643,276 | 7/1997 | Zaleski . |
| 5,735,858 | 4/1998 | Makker et al. . |
| 5,772,666 | * 6/1998 | Fiengold et al. ............. 606/107 |
| 5,860,984 | 1/1999 | Chambers et al. . |
| 5,868,752 | 2/1999 | Makker et al. . |
| 5,873,879 | 2/1999 | Figueroa et al. . |

FOREIGN PATENT DOCUMENTS

| | | | |
|---|---|---|---|
| 405103809 | 4/1993 | (JP) | ................ 606/107 |
| 9513022 | 5/1995 | (WO) . | |
| 9521594 | 8/1995 | (WO) . | |
| 9522287 | 8/1995 | (WO) . | |

* cited by examiner

*Primary Examiner*—Paul J. Hirsch
(74) *Attorney, Agent, or Firm*—Stout, Uxa, Bryan & Mullins; Frank J. Uxa

(57) ABSTRACT

Apparatus for inserting intraocular lenses (IOLs) into eyes comprises a tube, a rod having a distal end portion, and a tip carried by the distal end portion. The tip is softer than the distal end portion of the rod. Methods for inserting an IOL into an eye using such apparatus are within the scope of the present invention.

12 Claims, 3 Drawing Sheets

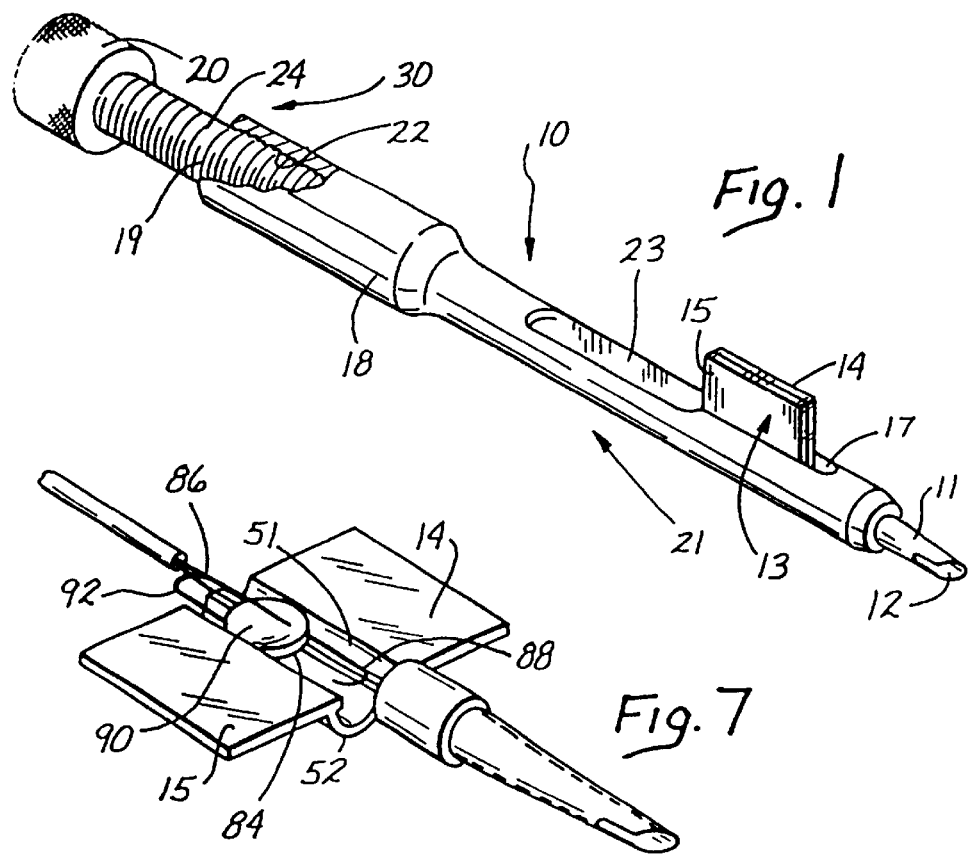
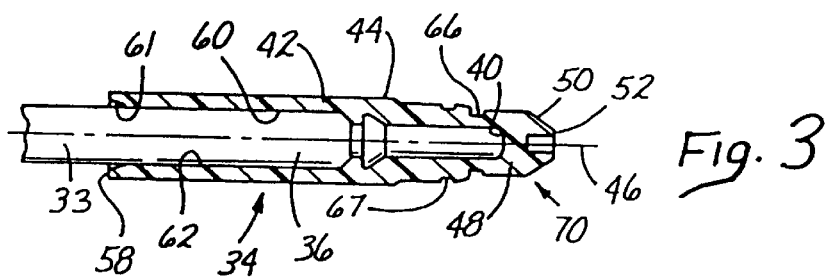
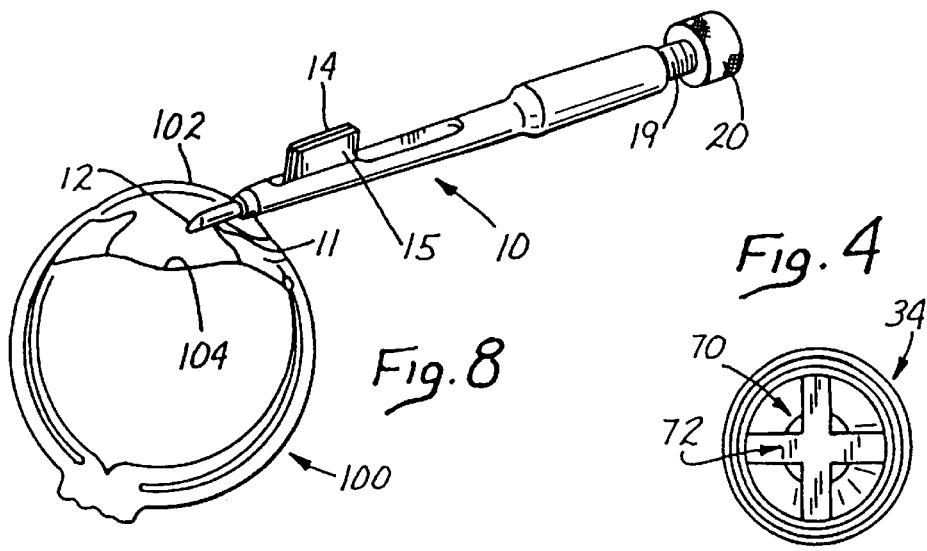

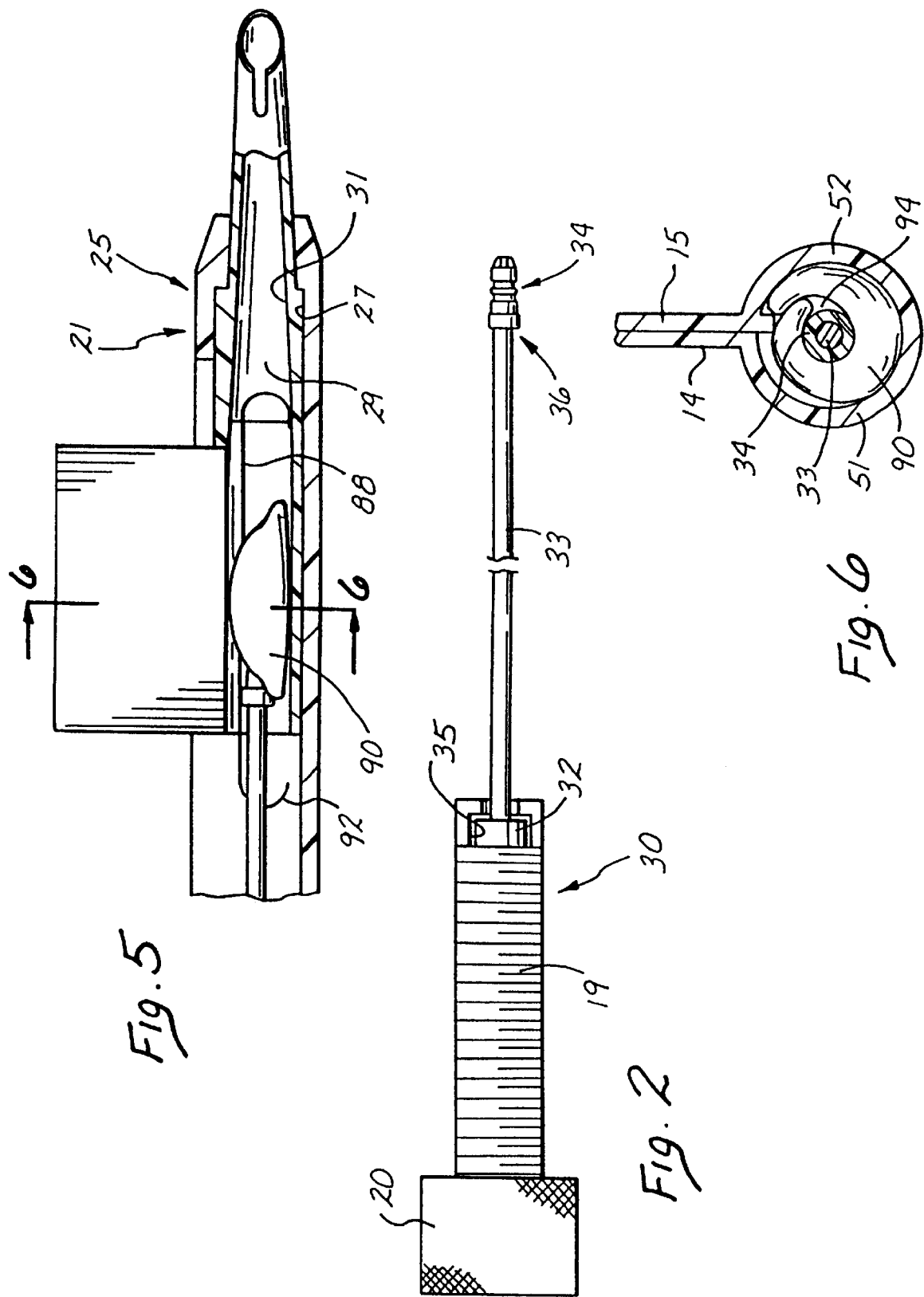

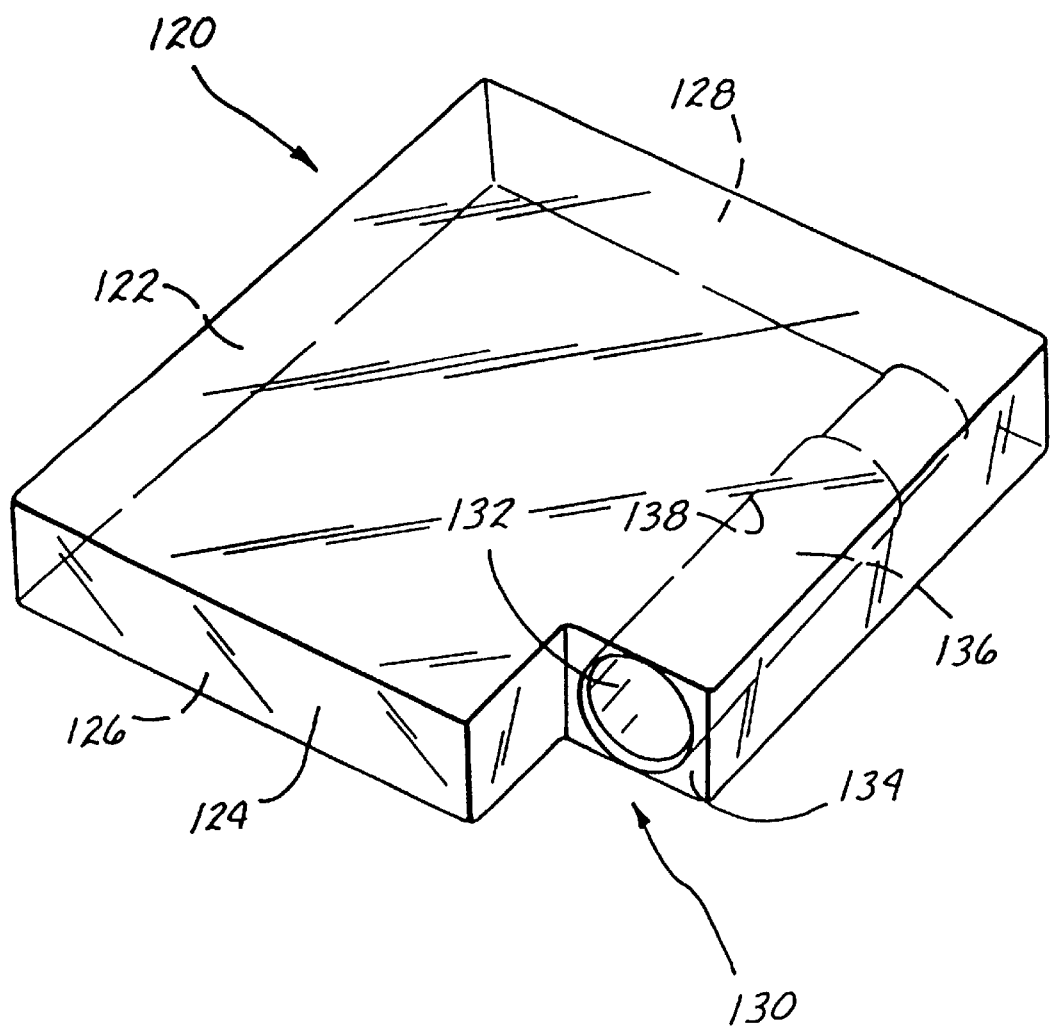

IOL INSERTION APPARATUS AND METHOD FOR USING SAME

This is a divisional application of application Ser. No. 09/253,639 filed Feb. 19, 1999, now U.S. Pat. No. 6,093,793 which, in turn, is a divisional application of application Ser. No. 08/864,296 filed May 28, 1997, now U.S. Pat. No. 5,876,407 which, in turn, is a divisional application of application Ser. No. 08/592,753 filed Jan. 26, 1996, now U.S. Pat. No. 5,735,858.

BACKGROUND OF THE INVENTION

The present invention relates to apparatus and methods for inserting an intraocular lens into an eye. More particularly, the invention relates to such apparatus and methods wherein the desired insertion of the lens is easily, controllably and effectively achieved.

An intraocular lens (IOL) is implanted in the eye, for example, as a replacement for the natural crystalline lens after cataract surgery or to alter the optical properties of (provide vision correction to) an eye in which the natural lens remains. IOLs often include an optic, and preferably at least one flexible fixation member or haptic, which extends from the optic and becomes affixed in the eye to secure the lens in position. The optic of the IOL normally includes an optically clear lens. Implantation of such IOLs into the eye involves making an incision in the eye. Making the incision as small as possible reduces trauma and speeds healing.

IOLs are known which are foldable (deformable) so that the IOL can be inserted into the eye through an incision smaller than the diameter of the lens and subsequently permitted to unfold after it has passed through the incision. A substantial number of instruments have been devised to aid in inserting such a foldable lens into the eye. The advantages of the foldable lens in cataract removal and lens replacement are so significant that many of the lens replacement procedures are performed with folded lenses inserted into the eye, and released therein to assume their initial unfolded state.

Some of the most generally accepted insertion apparatus employ a hollow insertion tube having a diameter which permits the folded IOL to pass through the hollow space defined by the tube without permanent deformation, and a plunger assembly including a rod, often made of metal, which is moved longitudinally in the hollow space in contact with the optic of the IOL to push the IOL through the hollow space.

Several disadvantages are apparent in such insertion devices. For example, pushing, without trapping or holding, the IOL through and out of the hollow space defined by the tube can cause the IOL to be released from the insertion device without precise control, so that the released IOL may damage the eye and/or may be mispositioned in the eye. In addition, the metal rod can result in marking the surface of the optic and/or even tearing the optic, particularly when the optic is made of soft materials, such as soft elastomeric silicone polymeric materials. Also, the metal rod has a tendency to by-pass the IOL in the hollow space. That is, the rod as it is being moved distally through the hollow space may actually pass through a fold in the folded optic. If this occurs, the rod becomes ineffective to push the IOL through the hollow space. This problem has been avoided in the past by increasing the cross-sectional area of the rod. However, a rod with a large cross-sectional area presents its own problems. For example, pushing such a large rod through the hollow space can damage the IOL and/or the inserter or result in an uncontrolled release of the IOL into the eye, possibly with inserter debris being disadvantageously introduced into the eye.

Stoy et al U.S. Pat. No. 4,919,130 discloses a rod-type IOL insertion device including two separate rods. This patent discloses a cup-shaped head of soft material, such as a silicone elastomer, detachably connected at the distal end of the second rod which pushes a compressed IOL through the cannula or tube. Although this cup-shaped head may avoid scratching or tearing the lens during the pushing operation, its cup-shaped distal face does nothing to increase the control the surgeon has in releasing the IOL in the eye. In addition, this cup-shaped head is relatively short, in the axial direction, which can result in the head becoming separated from the rod in the eye. This can result in an additional procedure to remove the head from the eye, which is traumatic for the patient.

It would be advantageous to provide IOL insertion apparatus and methods which facilitate the passage of a folded IOL through the apparatus and the insertion of the IOL in the eye in an easy, effective and controlled manner while avoiding damage to the IOL and undue trauma to the patient.

SUMMARY OF THE INVENTION

New apparatus for inserting IOLs and methods for inserting IOLs into eyes have been discovered. The present apparatus and methods solve one or more of the problems of the prior art systems, such as those problems noted above. The present apparatus enable the surgeon to achieve a desired degree of control as the IOL is released from the apparatus, thus allowing for the use of effective, reliable, and non-excessive amounts of force to insert a folded IOL into an eye. The risk of tearing or otherwise damaging the IOL, and particularly the optic of the IOL, during insertion is advantageously reduced. The present invention is straightforward, easy to make and practice, and involves little or no modification of existing surgical techniques. Also, the IOLs do not need to be modified to accommodate the present apparatus and methods.

In one broad aspect, the present invention comprises apparatus for inserting IOLs into an eye which include a tube defining a hollow passage, for example, through at least a portion of which a folded intraocular lens can be moved. This tube has a port, preferably at its distal end, through which the IOL is passed from the hollow passage into an eye. A rod is also included, is longitudinally movable within the hollow space of the tube and includes a distal end portion. A tip is carried by the distal end portion of the rod and is softer, preferably more elastic, than the distal end portion. The rod may be made of a metal, a relatively rigid or non-elastic polymeric material or combinations thereof. The tip is preferably made of a polymeric material, particularly an elastomeric polymeric material, such as an elastomeric silicone polymeric material.

The tip in accordance with the present invention may be of any suitable configuration, provided that it functions as described herein. The tip preferably has a configuration such that (1) at least a portion of the tip is trapped or held by the IOL (the IOL may be considered to be trapped by the tip); and/or (2) the tip does not bypass the IOL during the insertion process; and/or (3) the tip does not cause significant or undue damage to the IOL. More preferably, at least two of these criteria are met, and still more preferably all three of the criteria are met.

In one very useful embodiment, the tip is sized and configured so that at least a portion of the tip, preferably at least about 20% or at least about 30% of the length of the tip, is introduced into, and preferably held in, a fold of the folded IOL, preferably the folded optic of the folded IOL, as the rod is moved distally in the hollow space of the tube. For example, with a tip having a length of about 4 mm to about 10 mm, about 1.5 mm to about 5 mm of the length of the tip may be introduced into a fold of the folded IOL as the rod is moved distally in the hollow space of the tube. This feature of the present invention preferably results in the folded IOL being passed through the hollow space of the tube other than by pushing, even though the rod and tip are being moved distally. The folded IOL can be considered as being carried by and/or pulled by the rod/tip combination. The advantage of this non-pushing mode of passing through the hollow space is increased control. That is, the surgeon has an increased degree of control, relative to pushing the IOL through the hollow passage, of the movement of the IOL through the hollow passage of the tube and the release of the IOL into the eye.

The present tip may, and preferably is, adapted to fit onto the distal end portion of the rod and has a proximal end region having an outer surface which defines a cross-sectional area which is larger than the cross-sectional area defined by the outer surface of any other region of the tip. The proximal end region of the tip preferably is larger in cross-sectional area than is the distal end region of the tip. This feature, which may be considered to be a distal tapering of the tip, allows the tip to more effectively and efficiently enter a fold of the folded IOL and to become held or trapped by the folded IOL. A particularly useful embodiment provides that the distal end region defines a smaller cross-sectional area than does that defined by the outer surface of the proximal end. Very effective results are obtained by providing the tip with a proximal end region which is substantially tapered. For example, at least a portion of the tip which extends distally beyond the rod may have a generally conical or truncated conical configuration which facilitates the introduction of the tip into a fold of the folded IOL.

The tip of the present apparatus is preferably sufficiently elongated so that when the tip is being held in a fold of the folded IOL the optic of the folded IOL is not in direct contact with the rod. That is, for example, the tip has sufficient length so that the optic of the folded IOL comes in direct contact only with the tip as the rod is moved distally in the hollow space defined by the tube. This feature provides substantial benefits, for example, in that the optic is prevented from contacting the rod, which may cause scratching or tearing of the optic. Excellent results are obtained with a tip having a length in the range of about 1 mm to about 5 mm or 10 mm or about 50 mm, although other lengths may be suitable.

One important advantage of the present system is that the rod of the present apparatus may have a cross-sectional area which is reduced relative to a similar apparatus without the tip configured so that the rod of the similar apparatus directly contacts the folded IOL as the rod is moved distally in the hollow space defined by the tube. To illustrate, without the present tip, the rod of the apparatus must be sufficiently large, in cross-section, so that the rod does not bypass the lens as it is moved distally. As noted above, such bypassing results in the folded IOL not being pushed distally toward the eye. By making the rod sufficiently large, no bypassing can occur. One disadvantage of such a large rod is that it may be more difficult to pass through the hollow space of the tube, which hollow space is quite small because there is often the need to pass the distal end of the tube through an incision into the eye. Also, relatively large rods have a tendency to damage, for example, crack, the optics of the IOLs being inserted and/or result in an uncontrolled release of the IOL into the eye.

With the tip, the rod can be reduced in cross-sectional area since the tip is preferably configured to be introduced into a fold of a folded IOL and to be held in such fold. Also, because the tip is at least somewhat flexible or compliant, it is easily passed through the hollow space defined by the tube. The relatively large frictional forces between the tip and the folded IOL together with the relatively large degrees of deformability of both the tip and the folded IOL also contribute to allowing the use of a rod having a reduced cross-sectional area. These factors are particularly important when both the tip and the optic of the IOL are made of elastomeric silicone polymeric materials. With the tip in place, the cross-sectional area defined by the outer surface of the rod can be reduced, thereby making it easier to pass the rod through the hollow space defined by the tube.

Although the present insertion systems may be employed with any foldable or deformable IOL, they are particularly useful with such IOLs which have optics made of elastomeric silicone polymeric materials. This is so, for example, because such silicone-based IOLs very rapidly regain their original shape after being inserted in an eye in a folded condition. Thus, it is important with such silicone-based IOLs that the release of the IOL from the insertion apparatus be controlled to facilitate proper positioning of the IOL in the eye. Other IOLs, for example, IOLs including optics made of acrylic-based polymeric materials, regain their original configuration relatively slowly after being inserted in an eye in a folded condition. This "dampened" unfolding allows the surgeon more time to properly position the IOL in the eye after insertion so that controlled release of such IOLs from the inserter is somewhat less important.

In another broad aspect of the present invention, methods for inserting an IOL into an eye are provided. Such methods comprise:
  placing an IOL in a folded condition in an insertion apparatus comprising a tube defining a hollow passage and having a port through which the IOL is passed from the hollow passage into the eye, a rod longitudinally movable within the hollow passage and having a distal end portion, and a tip carried by the distal end portion and being softer and/or more elastic than the distal end portion;
  moving the rod distally thereby introducing at least a portion of the tip into a fold of the folded IOL;
  positioning the port in proximity to or in the eye; and
  passing the IOL through the hollow space or passage, through the port and into the eye.

The passing of the folded IOL through the hollow space preferably occurs with at least a portion of the tip held in a fold of the folded IOL.

Insertion apparatus as disclosed elsewhere herein are particularly useful in practicing the present methods. An important advantage of the present method is that the IOL can be passed into the eye through an incision in the eye no larger than about 3.5 mm, and more preferably no larger than about 3.0 mm.

Each of the individual features of the present invention disclosed herein may be used alone or in combination with one or more other of such features, provided such features are not mutually inconsistent with each other. All apparatus and methods involving any such feature or combinations of such features are included within the scope of the present invention.

These and other aspects of the present invention will become apparent in the following detailed description and claims, particularly when considered in conjunction with the accompanying drawings in which like parts bear like reference numerals.

BRIEF DESCRIPTION OF THE DRAWINGS

FIG. 1 is a side perspective view of an insertion apparatus in accordance with the present invention.

FIG. 2 is a side view, partly in cross-section, of the rod-plunger assembly removed from the body of the insertion apparatus shown in FIG. 1

FIG. 3 is a side view, partly in cross-section, of the distal end region of the rod-plunger assembly shown in FIG. 2.

FIG. 4 is a front view of the rod-plunger assembly shown in FIG. 2.

FIG. 5 is a side elevation view, partly in cross-section, of the insertion apparatus shown in FIG. 1 with the tip introduced into a fold of the IOL to be inserted into an eye.

FIG. 6 is a cross-sectional view taken generally along line 6—6 of FIG. 5.

FIG. 7 is a perspective view of a folding device shown in the open position.

FIG. 8 is a schematic perspective view showing the placement of the distal portion of the insertion tube in an eye.

FIG. 9 is a top front prospective view showing a carrier system for the tip in accordance with the present invention.

DETAILED DESCRIPTION OF THE PREFERRED EMBODIMENTS

FIG. 1 illustrates an IOL insertion apparatus, shown generally as 10. The apparatus 10 comprises body 21, and a folding cartridge 13 including a forward tube 11 having an open port 12 at its distal end. The body 21 of injection apparatus 10 is an integrally formed unit. Folding cartridge 13 has folding leaves 14 and 15 which extend through opening 17 in the outer wall of the body 21. Proximal end portion 18 can be sized to completely and closely encompass plunger 19 of rod-plunger assembly 30, which has a plunger cap 20 affixed to its proximal end.

Proximal end portion 18 is hollow and includes a threaded surface 22, the threads of which matingly engage the threads 24 on the outer surface of plunger 19.

Insertion apparatus 10 includes a slot 23 which extends from the proximal portion of opening 17 and connects therewith. Slot 23 is elongated in a direction parallel to the longitudinal axis of insertion apparatus 10. Slot 23 is sufficiently wide to permit the closed folding members 51 and 52, shown in FIGS. 6 and 7, to fit therethrough, and sufficiently long to permit loading cartridge 13 to be inserted therein, so that the folding cartridge can be subsequently moved into connecting opening 17, which is sufficiently narrow to hold the folding cartridge in a fully closed position.

As shown in FIG. 5, the distal end portion 25 of body 21 is hollow. When loading cartridge 13 is inserted into body 21, as shown in FIG. 5, the hollow space defined by the inner wall 27 of the body 21 is aligned with the hollow space 29 defined by the inner wall 31 of the loading cartridge 13. The combination of the joined body 21 and cartridge 13 can be considered a hollow tubular member defining a hollow space through which the rod 33 can pass longitudinally.

FIG. 2 shows injector rod-plunger assembly 30 with locking enclosure 35 holding injector rod cap 32. Tip 34 is disposed on the distal end portion 36 of the rod 33. Tip 34 is made of an elastomeric silicone polymer composition which is softer and more elastic than rod 33 which is made of titanium. For example, tip 34 is made of a material having a Shore A Hardness value in the range of about 40 to about 80 or about 90 or higher, more specifically about 70 to about 75. Viewed from a different perspective, the tip 34 preferably has a Shore A Hardness value within about 30 of the Shore A Hardness value of the material for which the optic of the IOL to be inserted is made.

With reference to FIG. 3, tip 34 has a length in the range of about 2 mm to about 10 mm, for example 8 mm. The length of tip 34 beyond the distal end 40 of rod 33 is in the range of about 0.25 mm to about 1.0 mm, for example, about 0.75 mm. Tip 34 is generally tapered in the distal direction, with the proximal end region 42 having an outer surface 44 which defines a larger cross-sectional area (transverse to longitudinal axis 46) than any other region of the tip. In addition, the distal end region 48 has an outer surface 50 (which extends to the distal end 52 of tip 34) which defines a smaller cross-sectional area than that defined by the outer surface 44 of the proximal end region 42.

Tip 34 includes an irregularly shaped inner surface 60 which defines an irregularly shaped blind bore in which is located the distal end portion 36 of rod 33. The blind bore defined by inner surface 60 is open at the proximal end 58 of tip 34. The inner surface 60 is configured to mate with the outer surface 62 of the distal end portion 36 of rod 33. Inner surface 60 includes a slightly enlarged flared section 61 which facilitates placing the distal end portion 36 of the rod 33 into the blind bore defined by the inner surface. Tip 34 includes distal annular indents 66 and 67 which are effective in facilitating introducing the tip into a fold of a folded IOL and in facilitating holding the tip in the fold of the IOL. In general, the outer surface of the tip in accordance with the present invention preferably is configured, such as with indents 66 and 67, to facilitate holding or trapping at least a portion of the tip in a fold of the IOL.

With the outer surface 62 of the distal end portion 36 of rod 33 mated to the inner surface 60 defining the blind bore, tip 34 is secured to rod 33. Tip 34 can be manually placed on the distal end portion 36 of rod 33. The distal end region 48 of tip 34 includes a slotted truncated cone structure 70. A cross slot 72 is placed in the truncated cone structure 70. This feature facilitates introducing the tip 34 into a fold of an IOL as the rod and tip combination is moved distally in the hollow space of a tube, as is described hereinafter. However, it should be noted that this slot structure 72 and the truncated cone structure 70 are not necessary in order to achieve substantial benefits in accordance with the present invention.

FIG. 7 illustrates the manner in which lens cartridge 13 produces the desired result of folding IOL 37. Hinged folding leaves 14 and 15 are used to open and close folding members 51 and 52, respectively. IOL 84 (in an unfolded state) is placed on folding members 51 and 52, by forceps 86. The forceps 86 hold the IOL 84 in a specific and determinable planar orientation. Superior haptic 88 is placed forward of optic 90, while the other haptic 92 trails the optic, as shown in FIG. 5. Hinged folding leaves 14 and 15 are moved together, which folds the flexible or foldable optic 90 of IOL 84 in half. After IOL 84 is folded, the forceps 86 is removed.

The closed loading cartridge 13, containing the folded IOL 84, is then loaded into body 21 of insertion apparatus 10, as described above. An effective amount of a lubricant composition, such as a visco-elastic material, for example, a conventional sodium hyaluronate-containing aqueous material or the like, is preferably included in the hollow space defined by the loading cartridge 13. This lubricant composition allows the folded IOL 84 to more easily pass through the hollow space defined by the loading cartridge 13.

Insertion apparatus 10 is operated and functions as follows. When it is desired to insert IOL 84 into an eye, the apparatus 10 is placed in a configuration as shown in FIG. 1, with tip 34 secured to rod 33, as shown in FIG. 2.

With the IOL 84 in its folded condition within apparatus 10, the operator (surgeon) advances plunger 19 distally by rotating cap 20. This action advances rod 33 and tip 34 distally. As rod 33 and tip 34 are moved distally, the tip comes into contact with folded optic 90 and is introduced into the fold 94 of the folded optic as shown in FIGS. 5 and 6. Because of the relative softness and elasticity of tip 34, the distal movement of rod 33 and the tip causes the tip to become trapped in the fold 94. The folded optic 90 can be considered to be pulled or carried by the rod 33 and tip 34 when the tip is trapped in the fold 94.

Referring now to FIG. 8, the IOL 84 is to be placed in eye 100 into an area formerly occupied by the natural lens of the eye. With the IOL 84 in its folded position within apparatus 10, and tip 36 trapped in fold 94, forward tube 11 is ready for insertion through an incision in the sclera 102 of eye 100. Capsular bag 104 protects the posterior segment of the eye 100. With the forward tube 11 inserted within the eye 100 and the port 12 positioned so that the IOL 84 can unfold in the location within the eye 100 best suited for permanent implantation, the operator advances plunger 19 by rotating cap 20. This action advances, rod 33, tip 36 and IOL 84 distally into the forward tube 11.

As rod 33 advances farther distally, the IOL exits the port 12 in a controlled manner and is controllably released in a location as close as possible to the IOL's final implanted position.

FIG. 8 shows the sclera 102 having an incision through which the distal end portion of forward tube 11 is passed. Alternately, the incision can be made through the cornea or other portion of the eye. Forward tube 11 has a sufficiently small cross-section to pass into the eye 100 through a 3.0 mm incision in the sclera 102. Folding leaves 14 and 15, in contact with each other when lens folding cartridge 13 is in a closed position, can be grasped by an operator and used to guide and position insertion tube 11 in its desired position within the eye.

After IOL 84 has been inserted into eye 100, forward tube 11 is removed from the eye. The tip 34 can be used to position the IOL 84 in the eye. For example, the tip 34 can be retracted (after the optic is released) and then used to push the trailing haptic 92 out of the tube 11 and position this haptic into the eye. If needed, IOL 84 can be repositioned in the eye by a small, bent needle or similar tool inserted into the same incision.

Once IOL 84 is properly positioned in eye 60 and apparatus 10 is withdrawn from the eye, the incision in the sclera may be closed, for example, using conventional techniques. After use, folding cartridge 13 and tip 34 are preferably disposed of. Remaining portions of apparatus 10 can be reused after sterilization and disinfection.

FIG. 9 shows a tip holder, shown generally at 120, which includes a top surface 122, a bottom surface 124, a front surface 126 and a back surface 128. Front surface 126 includes an indent 130 at one end thereof. Indent 130 includes a forward-facing surface 134 which includes an opening 132. A closed bore 136 is located within the body of tip holder 120 and is open at opening 132. Closed bore 136 has a sidewall configuration 138 which corresponds substantially to the outer surface of the tip 34, with the distal end of the tip being placed furthest into closed bore 136. The tip holder 120 may include a plurality of closed bores, such as closed bore 136, each of which adapted to be provided with a different tip, such as tip 34. With multiple closed bores, this tip holder 120 can be used to apply a tip to a plurality of rods.

In use, tip carrier 120 is provided with tip 34 within closed bore 136. Tip carrier 120 is sized so as to be conveniently held in the hand of a human being. When it is desired to apply the tip 34 from carrier 120 onto the rod 33, the rod 33 is inserted into the closed bore 136. In so doing, the tip 34 becomes secured to the rod 33. Thus, as the rod 33 is removed from closed bore 136, the tip 34, secured to rod 33, is also removed from the closed bore. At this point, rod 33 and tip 34 are ready for use, as described elsewhere herein. The tip carrier 120, which is preferably made of a substantially rigid, transparent polymeric material, can be reused, after sterilization, or, and preferably, is disposed of after a single use.

Other structures may be employed to facilitate applying the tip to the rod. For example, an elongated member with the tip secured to its distal end portion can be provided. The elongated member has sufficient length to be conveniently held in the hand of a human user. The proximal end portion of the elongated member is removably coupled to the rod, for example, using a "snap-on" arrangement, a friction or interference fit, mutually engagable threads on both the rod and elongated member or the like. Alternately, the loading cartridge can be provided with a tip holder, for example, integrally formed at the distal end of the cartridge. The tip is included in the holder during the manufacturing process. In use, the rod "picks up" the tip from the holder as the rod is moved distally into the hollow space defined by the cartridge. After the IOL is inserted, as the rod is moved proximally from the hollow space, the tip holder is configured to facilitate removing the tip from the rod. The cartridge and tip can than be disposed of, while the remainder of the apparatus can be reused after sterilization.

The disclosure of commonly assigned, U.S. patent application Ser. No. 08/592,163, now U.S. Pat. No. 5,776,138, filed on even date herewith is incorporated by reference in its entirety herein.

The following non-limiting examples illustrate certain aspects of the present invention.

EXAMPLES

A series of tests were run to evaluate the effectiveness of the tip design substantially as shown in the drawings.

The tips employed were substantially as shown in the drawings and were molded from a silicone polymeric elastomer made from a formulation sold by NuSil Technology under the trademark Nusil 4516. The tips were tinted blue to allow easy monitoring of the presence and location of the tips. The proximal ends of the tips had diameters of 1.40 mm and 1.52 mm, and a tip length of 3.43 mm. With the system used, a metal rod having a diameter of 1.54 mm would be required to push the lens out of the distal port of the forward tube.

Except for the presence of the tip, the system used in this testing was the IOL injector system sold by Allergan, Inc. under the trademark PIC 1. The lenses used in the testing had varying optical powers and included optics made of elastomeric silicone-based polymeric materials. Specifically the IOLs were those sold by Allergan, Inc. under the trademarks SI-30 and SI-40.

The test procedure used was as follows. The IOL was loaded into the loading chamber and the cartridge was placed into the hand piece. An amount of commercially available sodium hyaluronate-containing aqueous solution approximately equal to the volume of the IOL optic was dispensed into the loading chamber. In certain tests the IOL was immediately advanced through the entire forward tube and then out the distal port. In other tests, the IOL was advanced into the forward tube and allowed to dwell for a specified period of time before being released out the distal port. After the IOL was released, the rod and tip were cleaned with water and the tip was reused up to five (5) times.

Results of these tests were as follows:

| TEST | LENS | POWER, DIOPTERS | DWELL TIME, MINS. | RELEASE* | FORCE REQUIRED | IOL CRACKING |
|---|---|---|---|---|---|---|
| 1 | SI-30 | 20.0 | 0 | 1 | LOW | NONE |
| 2 | SI-30 | 20.0 | 0 | 1 | LOW | NONE |
| 3 | SI-30 | 23.0 | 0 | 2 | LOW | NONE |
| 4 | SI-30 | 18.5 | 0 | 1 | LOW | NONE |
| 5 | SI-30 | 6.0 | 0 | 2 | LOW | NONE |
| 6 | SI-30 | 12.0 | 0 | 1 | LOW | NONE |
| 7 | SI-30 | 21.0 | 0 | 1 | LOW | NONE |
| 8 | SI-30 | 30.0 | 0 | 1 | LOW | NONE |
| 9 | SI-30 | 23.0 | 0 | 1 | LOW | NONE |
| 10 | SI-30 | 27.0 | 0 | 2 | LOW | NONE |
| 11 | SI-40 | 22.0 | 1 | 1 | LOW | NONE |
| 12 | SI-40 | 22.0 | 1 | 2 | LOW | NONE |
| 13 | SI-40 | 22.0 | 1 | 2 | LOW | NONE |
| 14 | SI-40 | 22.0 | 1 | 2 | LOW | NONE |
| 15 | SI-40 | 22.0 | 1 | 2 | LOW | NONE |
| 16 | SI-40 | 22.0 | 1 | 2 | LOW | NONE |
| 17 | SI-40 | 12.0 | 1 | 2 | LOW | NONE |
| 18 | SI-40 | 22.0 | 1 | 2 | LOW | NONE |
| 19 | SI-40 | 12.0 | 1 | 1 | LOW | NONE |
| 20 | SI-40 | 22.0 | 1 | 1 | LOW | NONE |
| 21 | SI-40 | 22.0 | 2 | 2 | LOW | NONE |
| 22 | SI-40 | 22.0 | 2 | 2 | LOW | NONE |
| 23 | SI-40 | 12.0 | 2 | 2 | LOW | NONE |
| 24 | SI-40 | 12.0 | 2 | 2 | LOW | NONE |
| 25 | SI-40 | 22.0 | 2 | 2 | LOW | NONE |
| 26 | SI-40 | 22.0 | 4 | 2 | MODERATE | NONE |
| 27 | SI-40 | 22.0 | 8 | 2 | MODERATE | NONE |

*The release of the IOL out of the distal port was rated:
1. Very well controlled
2. Controlled, acceptable
3. Uncontrolled, not acceptable
4. IOL shoots out of port, not acceptable The IOL insertion system including a tip in accordance with the present invention was effective. For example, all of the IOLs tested exhibited acceptable releases, even after four (4) and eight (8) minute dwell times. In contrast, comparable tests using a metal rod without the tip provided instances where the IOL unacceptably shot out of the distal port. Also, no rod bypassing occurred. A substantial amount of rod bypassing occurred in comparable tests using a metal rod without the tip.

The plunger forces were low for all 0, 1 and 2 minute dwell time tests, and were moderate for the 4 and 8 minute dwell time tests. The amount of trapping, that is the length of the tip trapped or held by the folded IOL, varied from about 2 mm to about 4 mm. No cracking, chipping or tearing of the IOL optic was observed. Comparable tests using metal rods without tips resulted in "heavy" or substantial marking of the IOL optics.

The present IOL insertion apparatus and methods effectively and straightforwardly control the insertion and release of the IOL in the eye. This control is achieved without undue reliance on the technique and/or dexterity of the surgeon and without undue risk of damaging the IOL being inserted. Controlling the insertion of the IOL reduces the risk of damaging the IOL and components of the eye, and facilitates positioning the IOL in the eye in the desired location.

While this invention has been described with respect to various specific examples and embodiments, it is to be understood that the invention is not limited thereto and that it can be variously practiced within the scope of the following claims.

What is claimed is:

1. An apparatus comprising:
    a tip adapted to be carried by a distal end portion of a rod used to facilitate the insertion of an intraocular lens into the eye, the tip having an open proximal end, a proximal end region having a first outer surface, an opposing distal end region having a second outer surface, and an inner surface defining a blind bore that is open at the open proximal end and is adapted to receive the distal end portion of the rod, the second outer surface defining a smaller cross-sectional area than the first outer surface.

2. The apparatus of claim 1 wherein the tip is made of polymeric material.

3. The apparatus of claim 1 wherein the second outer surface includes at least one annular indent.

4. The apparatus of claim 1 wherein the first outer surface defines a cross-sectional area which is larger than the cross-sectional area defined by the outer surface of any other region of the tip.

5. The apparatus of claim 1 wherein the tip is made of elastomeric silicone polymeric material.

6. The apparatus of claim 1 wherein the tip includes a closed distal end.

7. The apparatus of claim 1 wherein the distal end region of the tip is distally tapered.

8. An apparatus comprising:

a tip adapted to be carried by a distal end portion of a rod used to facilitate the insertion of an intraocular lens into the eye, the tip having an open proximal end, a proximal end region having a first outer surface, an opposing distal end region having a second outer surface, and an inner surface defining a blind bore that is open at the open proximal end and is adapted to receive the distal end portion of the rod, the outer surface of the proximal end region defining a larger cross-sectional area than any other region of the tip.

9. The apparatus of claim 8 wherein the tip is made of polymeric material.

10. The apparatus of claim 8 wherein the tip has a distal end region having an outer surface with at least one annular indent.

11. The apparatus of claim 8 wherein the tip is made of elastomeric silicone polymeric material.

12. The apparatus of claim 10 wherein the tip includes a closed distal end.

* * * * *